(12) United States Patent
Fox et al.

(10) Patent No.: US 6,986,746 B2
(45) Date of Patent: Jan. 17, 2006

(54) BIASED VASCULAR TEMPERATURE MEASURING DEVICE

(75) Inventors: Stewart M. Fox, Cambridge (GB); Leonidas Diamantopoulos, Merelbeke (BE); Glenn Van Langenhove, Merelbeke (BE)

(73) Assignee: Thermocore Medical Systems NV (BE)

( * ) Notice: Subject to any disclaimer, the term of this patent is extended or adjusted under 35 U.S.C. 154(b) by 0 days.

(21) Appl. No.: 10/485,069

(22) PCT Filed: May 3, 2002

(86) PCT No.: PCT/GB02/02081

§ 371 (c)(1),
(2), (4) Date: Aug. 2, 2004

(87) PCT Pub. No.: WO03/011125

PCT Pub. Date: Feb. 13, 2003

(65) Prior Publication Data

US 2004/0260197 A1 Dec. 23, 2004

(30) Foreign Application Priority Data

Aug. 1, 2001 (EP) ............................................. 01306599
Dec. 11, 2001 (GB) ............................................. 0129647

(51) Int. Cl.
*A61B 5/00* (2006.01)

(52) U.S. Cl. ..................................................... 600/549
(58) Field of Classification Search ................ 600/549, 600/505, 585; 604/95, 96, 280–282; 374/179
See application file for complete search history.

(56) References Cited

U.S. PATENT DOCUMENTS

| 4,369,795 | A | * | 1/1983 | Bicher et al. ............... 600/549 |
| 5,769,830 | A | | 6/1998 | Parker |
| 5,782,239 | A | | 7/1998 | Webster, Jr. |
| 5,924,997 | A | | 7/1999 | Campbell |
| 6,053,937 | A | | 4/2000 | Edwards et al. |
| 6,712,771 | B2 | * | 3/2004 | Haddock et al. ............ 600/549 |
| 2002/0198465 | A1 | * | 12/2002 | Fox et al. ................... 600/549 |

FOREIGN PATENT DOCUMENTS

| EP | 0 856 278 A2 | 8/1998 |
| EP | 1 025 797 A1 | 8/2000 |
| WO | WO 81/03607 | 12/1981 |
| WO | WO 00/27278 | 5/2000 |

* cited by examiner

*Primary Examiner*—Max F. Hindenburg
*Assistant Examiner*—Brian Szmal
(74) *Attorney, Agent, or Firm*—Bromberg & Sunstein LLP

(57) ABSTRACT

The present invention provides a vascular catheter apparatus for temperature measurement of vascular tissue, comprising a flexible body, at least one resiliently biased projection depended from the body, a sensor carried by the projection and an electrical carrier for transmitting temperature data at the vascular wall from the sensor to a remote device. The electrical carrier may be coiled around the length of the projection to reduce the strain at critical points where it is necessary to maintain a seal and hence electrical isolation.

12 Claims, 4 Drawing Sheets

(1 of 4 Drawing Sheet(s) Filed in Color)

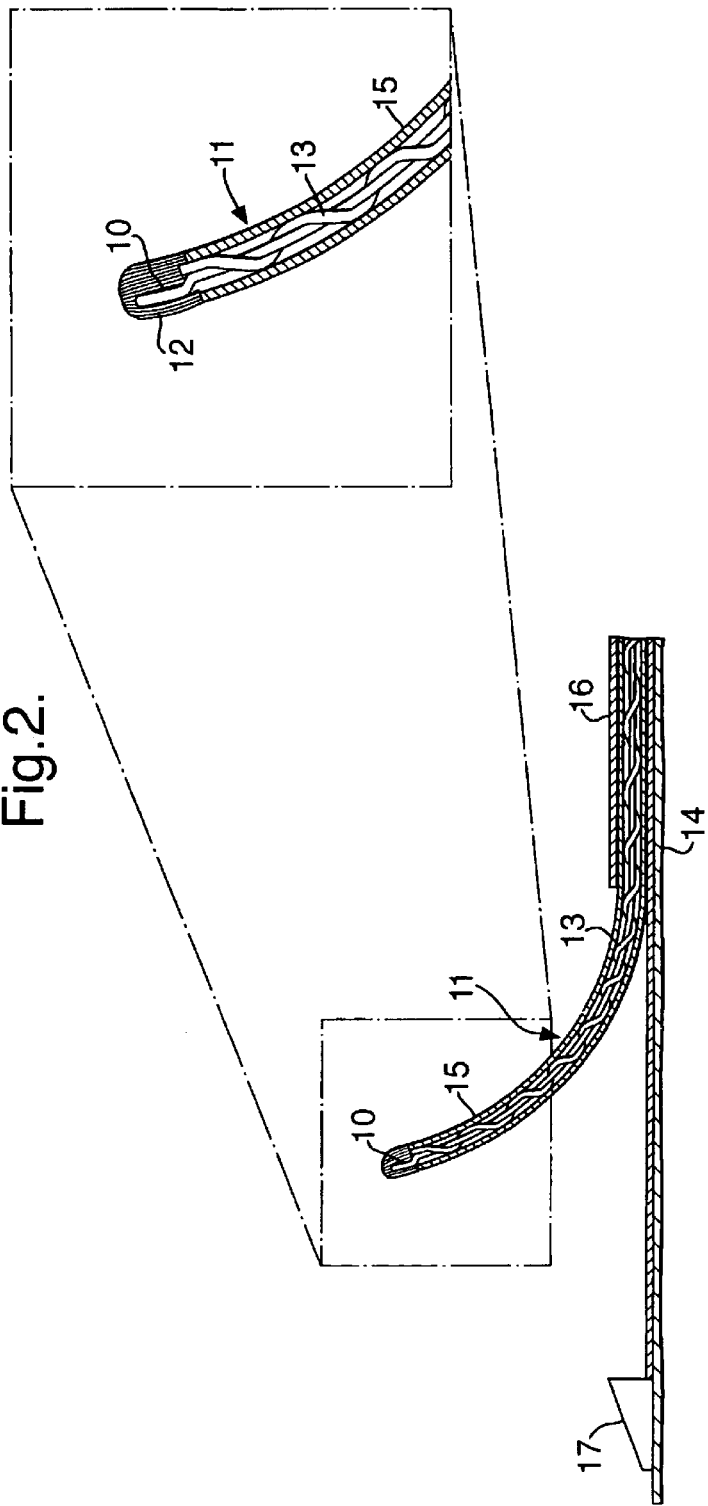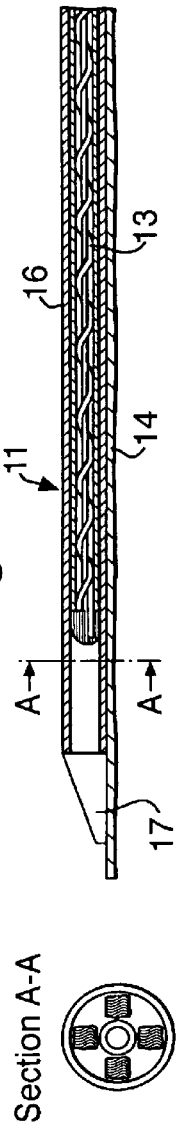

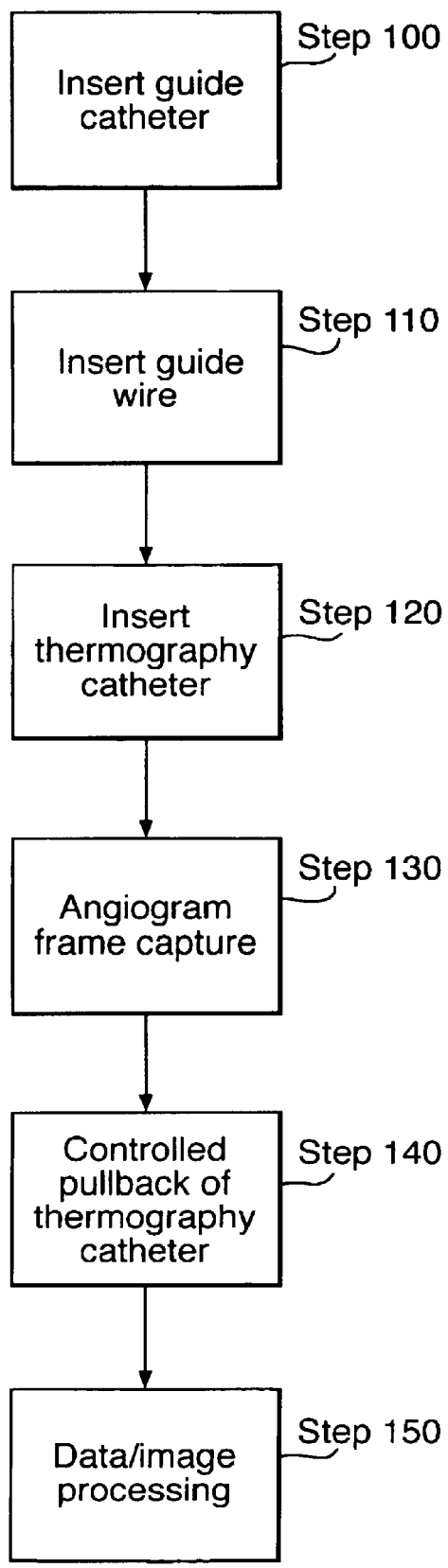

BIASED VASCULAR TEMPERATURE MEASURING DEVICE

FIELD OF THE INVENTION

The present invention relates to a medical device for measuring the temperature of vascular tissue. The present invention is particularly related to locating inflamed or unstable artherosclerotic plaque in a blood vessel.

BACKGROUND TO THE INVENTION

Plaque can develop in a patient's cardiovascular system. The plaque can be quite extensive and occlude a substantial length of the vessel. Additionally, the plaque may be inflamed and unstable, such plaque being subject to rupture, erosion or ulceration which can cause the patient to experience a myocardial infarction, thrombosis or other traumatic and unwanted effects. Furthermore, relative blood viscosity rises and aggregation of platelets increases with temperature increases (Dintefass L. Rheology of Blood in Diagnostic and Preventive Medicine. London, UK: Butterworths; 1976;66-74). Previous ex vivo studies have shown that there is indeed thermal heterogeneity in human carotid atherosclerotic plaques (Casscells W, Hathom B, David M, Krabach T, Vaughn W K, McAllister H A, Bearman G, Willerson J T. Thermal detection of cellular infiltrates in living atherosclerotic plaques: possible implications for plaque rupture and thrombosis. Lancet 1996;347:1447-1449).

An example of a vascular catheter, termed a thermography catheter, is described in our co-pending International patent application number PCT/EP 01/04401. The distal tip of the thermography catheter incorporates four sensors mounted circumferentially about a central lumen on resiliently biased projections. The sensors are NTC thermistors that are attached to the end of each projection by bonding with an thermally conducting epoxy glue. Each thermistor is connected to an insulated bifilar wire that provides an electrical connection with the proximal end of the device (not shown). The projections are made of NiTinol and take on the deployed configuration automatically due to their memory properties. The projections are mounted on the central lumen and sandwiched between the central lumen and an intermediate lumen. The point at which the projections meet the central/intermediate lumen terminus is sealed so that the components located between the central and intermediate lumen are electrically isolated from the patient. The thermography catheter is mounted on an angioplasty guide wire which runs through the central lumen and a guide member which defines the tip of the thermography catheter.

In use, the apparatus may be actuated between a deployed configuration and a retracted configuration. In the retracted configuration, a sheath encompasses the projections so that they are constrained to lie parallel to the longitudinal axis of the catheter and therefore cannot take up a deployed position. To adopt the deployed configuration, the sheath is withdrawn away from the extreme distal tip i.e., away from the guide member, towards the proximal section, to expose the projections. When the sheath is withdrawn the resiliently biased projections take up the deployed configuration. It should be noted that the sheath is controlled from the proximal end of the apparatus.

It is important to maintain electrical isolation between the electrical components and the patient. However, it has been found that the original design, described in International Patent Application No. PCT/EP01/04401, suffers from a form of fatigue (strain) failure caused by repeated shortening and lengthening of the electrical wires as the respective projections are deployed and retracted. Repeated compression and tensioning of the wire can cause a failure along the length of the wire and at the electrical connection to the thermistors and/or the sealed terminus between the central lumen and the intermediate lumen, causing an electrical short circuit in use.

SUMMARY OF THE INVENTION

According to the present invention, a catheter apparatus comprises a body, at least one resiliently biased projection depended from the body, a sensor carried by the projection, and an electrical carrier connected to the sensor for transmitting data from the sensor to a remote device, wherein the electrical carrier is coiled.

The present invention provides a catheter, preferably a vascular catheter, having one or more resiliently biased projections around which the electrical connection is coiled to reduce the strain at critical points where it is necessary to maintain a seal, and hence electrical isolation. The design is especially suitable for use as a thermography catheter of the type described in our earlier filed International patent application no. PCT/EP01/04401.

Preferably, the electrical carrier is coiled around the body of the projection.

Preferably, the pitch of the coil is arranged such that there are 5 to 10 turns per cm.

Preferably, a heat shrink wrapping is applied over at least a portion of the length of the projection. A heat shrink material is generally a polymeric material capable of being reduced in size upon application of heat. These are generally used in the form of a tube. Suitable materials include polyesters, PVC, polyolefins, PTFE and the like. The preferred material is a polyester.

Generally, the catheter comprises a plurality of co-axial lumen. Preferably, the catheter comprises a central lumen adapted to be mounted on a standard angioplasty guide wire suitable for vascular intervention. The apparatus is preferably based on the rapid exchange or the monorail system, although over-the-wire techniques are also envisaged. Preferably, outside the central lumen is located an intermediate lumen. Preferably, outside the intermediate lumen is mounted an external lumen, hereinafter referred to as a sheath. Preferably, at the distal tip of the apparatus is a guide member. Other lumen may be present and all the lumen may house components within themselves or between adjacent lumen.

The projection is preferably mounted on the central or intermediate lumen but may be attached to any lumen inside the sheath.

The central lumen may be formed from the standard catheter lumen materials, for example, nylon, FEP, polyurethane, polyethylene and nitinol and mixtures thereof.

The intermediate lumen and the sheath are generally constructed from, but individually selected from, the standard catheter lumen materials discussed above.

The sheath is adapted to fit over the adjacent lumen housed inside the sheath and should be able to move relative to the adjacent lumen under the control of a remote device.

Preferably, the central and intermediate lumen are bound to one another and are not moveable relative to one another.

Preferably, the flexible body of the catheter has a longitudinal axis and at least part of the projections are extensible radially from the longitudinal axis of the body. Generally, the projections have an elongate shape, preferably having dimensions in the range of 2 mm to 15 mm, more preferably 3 to 7 mm in length. The projections preferably have a caliper of 0.3 mm to 5 mm, more preferably 0.5 mm to 3 mm.

A first end of the projection is preferably attached to the body, preferably the intermediate and/or the central lumen, while a second end comprises one or more sensors. The second end is preferably free, ie, not attached to any of the lumen, and is adapted to be radially movable away from the central lumen.

Two or more sensors, preferably 2 to 10 sensors, more preferably 2 to 6 sensors may be utilised in the present invention. Preferably, each sensor is mounted on a separate projection. In a particularly preferred example, four projections, each having a single sensor mounted thereon, are provided. Where more than one projection is provided, each projection is preferably independently biased. Thus, each projection can follow the vessel morphology independent of the other projections.

The sensors are preferably located on an outer face of the projection, relative the central lumen, ie., facing the vascular tissue in use. Each sensor should preferably be located toward, or at the distal tip of the projection.

The projections need not be mounted in substantially the same circumferential plane of the catheter body, but this configuration is preferred.

It is also possible to provide projections having different lengths. This allows a better assessment of the 3D location of the arms to be provided while using a 2D imaging technique.

The projection preferably comprises a superelastic material. Superelasticity refers to the ability of certain metals to undergo large elastic deformation. Such compounds favorably exhibit features such as biocompatibility, kink resistance, constancy of stress, physiological compatibility, shape-memory deployment, dynamic interference, and fatigue resistance.

A large number of super-elastic materials may be utilised, particularly binary Ni—Ti with between 50 and 60 atomic percent nickel. While many metals exhibit superelastic effects, Ni—Ti-based alloys appear to be best suited for deployment in the human body due to them being chemically and biologically compatible.

Preferably, the projection, when not restrained will adopt a deployed configuration in which a free end of the projection is extended away from the central lumen. In this deployed configuration, the projection is resiliently biased against the vascular wall in use, thus initiating contact between the sensor and said wall. This achieves an adequate thermal contact with the vascular wall, without substantially compromising blood flow.

In accordance with a second aspect of the present invention and also a particularly preferred embodiment of the first aspect of the invention, the elongate projection, when restrained, adopts a substantially straight shape, which lies substantially parallel to the longitudinal axis of the catheter body. In the deployed configuration, the projection adopts an arcuate shape along at least part of its length. In this embodiment, the gradient of the arcuate portion of the projection, with respect to the longitudinal axis of the catheter, increases as a function of distance along the projection from the end attached to the catheter body. Thus, the free end of the projection bends away from the catheter body. This particular embodiment allows the sensor-bearing end of the projections to more accurately and consistently follow the morphology of the vascular tissue. A stenosis usually involves a section of the wall being inflamed and thus protruding into the lumen of the blood vessel. Alternatively, a calcified plaque may have an irregular surface leading to it protruding into the lumen. Where an arcuate deployed projection is employed, the arc allows the sensor bearing tip to "reach around" to the trailing edge of a stenosed region as the catheter is moved along the vascular tissue. The arcuate nature of the projections also allows the temperature sensors to be located more directly and in closer contact to the vessel wall. The maximum gradient of the projection, with respect to the longitudinal axis of the catheter body is preferably less than 90°, more preferably less than 75°, more preferably less than 60°. In this particular embodiment, the arc of the projection preferably provides maximum possible contact angle between the projection and the vessel wall of less than 90°, more preferably less than 75°, more preferably less than 60°. This angle, while having a maximum deviation of less than 90°, is variable as a consequence of the compliant nature of the biased projection. This allows the projection to follow the vascular morphology.

Where an arcuate projection is provided, there may also be substantially straight portions of the projection along its length.

In an alternative example, the projection may be mounted to achieve a similar resiliently biased effect. For example, one method of achieving this would be to mount the projection on a spring, preferably a micro-spring, such that when unrestrained, the projection is extended against the vascular wall as discussed above.

The sensors may be any form of temperature sensor and are preferably selected from thermistors, thermocouples, infra red sensors and the like. Preferably, the sensors are thermistors. These are preferably semi-conductor materials having an electrical impedance in the range of 1–50 KΩ. Such thermistors prove extremely reliable regarding the relation between the temperature changes and resistance changes.

Preferably, the thermography catheter comprises a radiopaque marker which aids in the location of the device by fluoroscopy during interventional surgery. More preferably, at least one sensor includes a marker so that it is discernible via fluoroscopy. Most preferably, individual sensors include different marker types, so that using fluoroscopy, the individual sensors can be identified and their spatial orientation and relative location to a desired part of the vessel wall thus clearly defined.

The distal tip may additionally comprise an ultrasound probe system that can give images of the arterial wall. This may be achieved by the incorporation to the distal catheter tip of a phased array of high-frequency ultrasonic crystals or a mechanical sector ultrasound element. In this way, intravascular ultrasound (IVUS) images may be captured simultaneously with the temperature data. This is extremely useful for morphological data acquisition, correctly recognizing the area of interest and for accurate catheter positioning.

The proximal section of the thermography catheter incorporates a connector for coupling the temperature data signals to a remote device such as a personal computer. These signals are transmitted along the wires from the sensors. The wires are preferably housed within the sheath and are preferably electrically isolated from the patient. Preferably, the wires are housed between the central lumen and the intermediate lumen, within the outer sheath.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Examples of the present invention will now be described in detail with reference to the accompanying drawings, in which:

FIG. 2 shows an enlarged partial section of an example of the distal tip of a thermography in accordance with the present invention in a deployed configuration;

FIG. 3 shows the catheter of FIG. 2 in a retracted configuration;

FIG. 4 is a flow diagram illustrating the steps involved with conducting intravascular catheterisation of a patient and the associated data capture and image processing; and, FIG. 5 shows an angiogram frame overlaid with a temperature profile.

DETAILED DESCRIPTION

Figure 1:
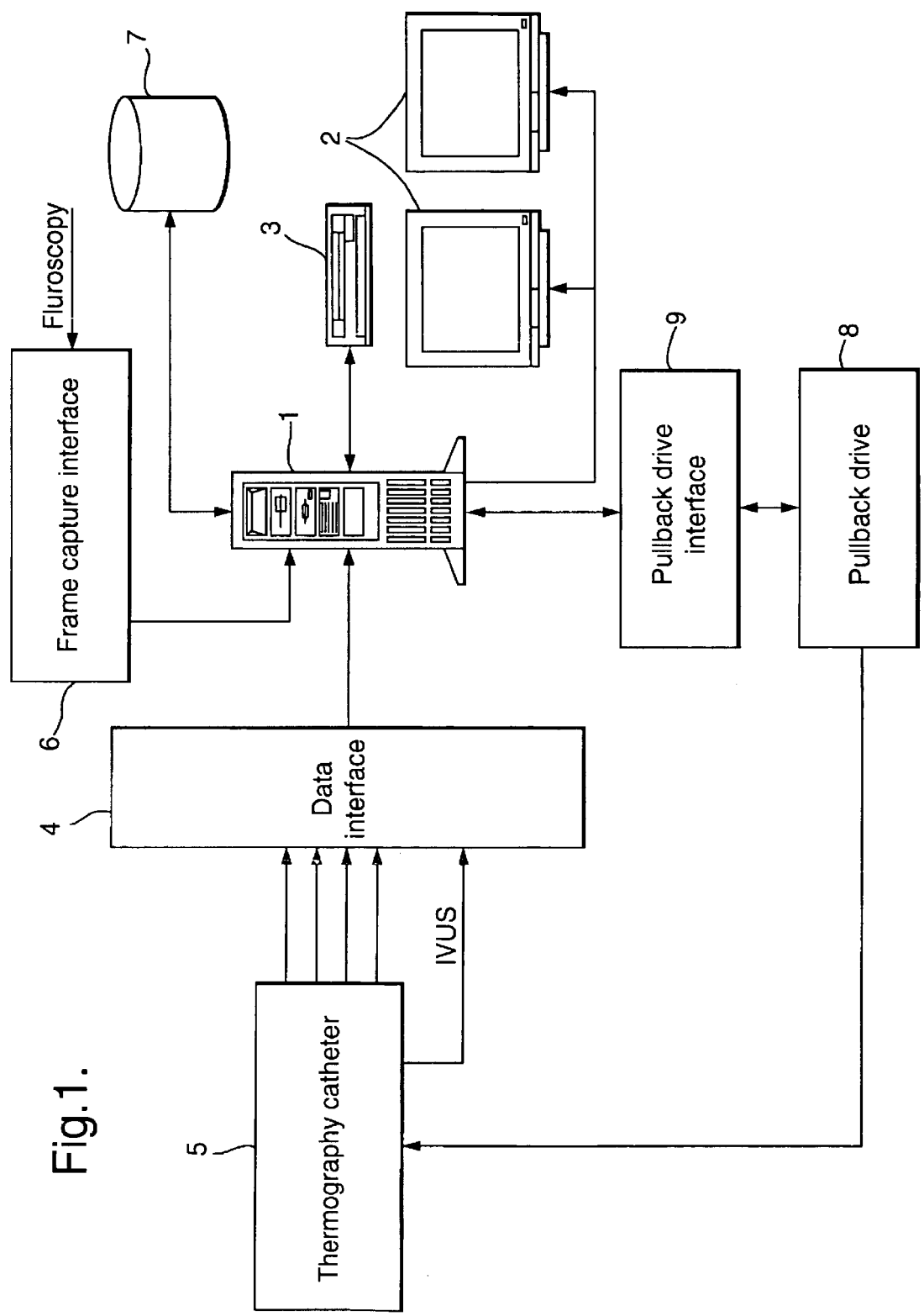
FIG. 1 shows a schematic diagram of a system for conducting vascular catheterisation of a patient.

FIG. 1 is a schematic diagram of a system for conducting vascular catheterisation of a patient.

The system includes a personal computer (PC) 1 that presents a graphical user interface (GUI) via a number of monitors 2. The user interface system is based on a Microsoft Windows™ platform. Multiple windows may be used to acquire/project data from/to the user. Although not shown, the PC can accept user inputs via a keyboard and mouse, or other pointing device, in the usual manner. The PC includes a number of data stores 7, which may be external, and a CD ROM reader/writer device 3.

The PC is coupled via a data interface 4 to a thermography catheter 5, details of which will be described below. In this example, the thermography catheter 5 transmits four channels (one for each sensor) which are received by the data interface 4. An analogue temperature data signal on each channel is converted to a digital signal using an A/D converter within the data interface 4 at a user configured sampling rate of up to 2.5 KHz. Typically, the sampling rate would be set at around 25 to 50 Hz to reduce the quantity of data acquired.

The data interface 4 includes a multiplexer (not shown) that combines the four digital channels into a single time division multiplexed (TDM) signal. This TDM signal is coupled to the PC over a PCI bus. The data from each channel are written into an area of memory within the data store 7 reserved for that channel where they can subsequently be retrieved for data processing along with the corresponding time sequenced data from other channels and image data from other sources.

The temperature data from the thermography catheter 5 are introduced to the system software running on the PC using function calls. Temperature data are input to the software as the actual voltage at the A/D hardware inputs, and therefore they have to be converted to temperature. A sensor data convert function handles this process.

The system is designed to be used in conjunction with a fluoroscopy x-ray apparatus and therefore includes a video frame capture interface 6 that couples fluoroscopy video data inputs to the PC via a PCI bus. Similarly, it can be used in conjunction with intravascular ultrasound (IVUS) image data fed from the thermography catheter 5 (when provided with the appropriate hardware). The system software allocates sufficient memory area to the systems memory for this data, taking into account the current system configuration, for example sampling rate, recording time, and video frame size. A memory handle hDib is used to map video data directly through the PCI bus from the video frame capture interface 6 to this allocated area in memory. hDib memory is divided into i equal chunks, each of a size equal to the frame capture interface frame-buffer. Optionally, hDib [i] in data can also be mapped to a memory area of a screen-video buffer, giving capability of live preview during recording. Each time the software records an x group of four (or more) temperature measurements, it prompts for a frame capture at hDib [x]. A user configuration file determines the ratio between temperature data:fluoroscopy video frame capture.

Whilst in normal circumstances the thermography catheter 5 is inserted manually, it is intended that when performing vascular measurements the thermography catheter 5 is pulled back relative to a predetermined start position using an electro-mechanical pull-back drive 8 coupled to the body of the catheter. The pull-back drive 8 is controlled by the PC via a pull-back drive interface 9. The system software accesses user-defined configuration files to get the necessary information about controlling the systems automatic pull-back interface 9. Data sampling rate, recording duration and pre-selected retraction rate are taken into consideration for adjusting the pull-back speed. The software routines control a D/A converter (not shown) that feeds the input of the pull-back interface 9 with an appropriate control voltage. The controlled pull-back process will be described in more detail below.

Temperature data plotting may be both on-line and/or off-line. In an on-line mode, the monitor presents a temperature/time-distance graph, where temperature is continuously plotted as connected dots. In an off-line mode, temperature data can be loaded from the data store 7 (or other media) and plotted on the screen graph. The user can scroll to different time/temperature locations, while several automated functions may be provided, for example auto min-max marking, colour coding of temperature on a bull-seye graph, colour thermal maps, and 3D temperature coding on a cylinder model. In the latter case, an artificial colour 3D cylinder that represents the vessel is divided into splines equal to the temperature channels. The channel temperature is coded on each spline with colours varying from dark-blue (minimum temperature) to flashing-red (maximum temperature). The user can rotate the cylinder as he wishes in a virtual 3D world. The focus is set to the specific time/distance that corresponds to the mouse position on the screen temperature/time graph. 3D position control is performed using multi cubic-bezier lines, where the curvation control points change in relation to the cylinders position in the virtual world. A separate window shows numeric details for the particular time/distance position. Video frame data from simultaneous fluoroscopy/IVUS are plotted as image frames in a separate window. By moving to a specific time/temperature position, the corresponding video frame is automatically projected. In this way, temperature and video frames are accurately synchronised.

The system software is designed to provide basic and advanced image processing functions for the captured fluoroscopy/IVUS video frames, such as filtering and on-screen measurement functions. The user can filter the captured frame to discard unwanted information while focusing on the desired one. There are several auto-filter options as well as manual adjustment of the image curve. In addition, the user can calibrate the system and proceed in performing on-screen measurements of both distances and/or areas. Automatic routines perform quantification of the measurements giving significant information on lesion characteristics. The temperature can also be colour coded on the fluoroscopy frame, providing unique information about the correlation between temperature and morphology.

By using temperature data and video frame data, the system software uses advanced algorithms based on interpolation and fractal theory to plot a 3D reconstruction of the vessel under measurement with colour coding of temperature. The user can freely move the virtual camera inside the reconstructed vessel in 360°, and/or fly-through the vessel. 2D reconstructions are also provided. Temperature data can be processed on the basis of mean temperature, or on a channel-by-channel basis.

FIGS. 2 and 3 show an example of the distal tip of a thermography catheter incorporating sensors 10 mounted circumferentially about a central lumen 14. In this example, four sensors 10 are mounted on resiliently biased projections 11 circumferentially about the central lumen at 90° intervals, although only one sensor is shown here for the sake of clarity. The projections 11 are made of NiTinol.

The figures clearly show the deployed configuration projection adopting an arcuate shape along its length, with the gradient of the projection, with respect to the longitudinal axis of the catheter, increasing as a function of distance along the projection from the end attached to the catheter body.

The sensors 10 are NTC thermistors. Such thermistors prove extremely reliable regarding the relation between the temperature changes and resistance changes. An NTC thermistor having a 30 KΩ impedance at 25° C. typically maintains linearity between 35° C. and 45° C., at a resolution of 0.01° C.–0.1° C.

The construction of the thermistors 10 are that of two rectangular plates with a metal alloy oxide in the centre. The thermistor has dimensions in the range of 0.25 mm–5 mm, and a caliper less than 1 mm.

Each thermistor 10 is attached to the end of each projection 11 by bonding with an thermally conducting epoxy glue 12. Each thermistor 10 is connected to an insulated bifilar wire 13. The wire 13 has a low impedance and is constructed from nickel and/or copper. This wire provides an electrical connection with the proximal end of the device (not shown).

As shown in the Figures, the wire 13 is coiled around the length of the projection 11. This feature has the effect of substantially eliminating strain when the projection 11 flexes. The pitch of the coil is typically arranged to be such that there are 5 to 10 turns over a length of 10 mm. As will be described below, a heat shrink wrapping 15 is applied over the projection 11 to prevent damage to the wire 13 during retraction and replacement of an outer sheath 16. The heat shrink wrapping also provides an additional degree of electrical isolation.

To assemble a projection, a NiTinol arm is first pretreated by placing it in a bending tool and heating to around 700° C. to impart a bend in the arm. The NiTinol arm is then held straight in a chuck and a thermistor/bifilar wire assembly is attached to a free end of the arm using a UV cure adhesive. The wire 13 is then spun around the length of the NiTinol arm. Finally, the heat shrink wrapping 15 is placed over the length of the NiTinol arm to a point just beyond that of the thermistor. In this example, the heat shrink wrapping is supplied as a polyester tube that is cut to length. An epoxy resin is then injected into the end of the tube. The assembly is subsequently heat treated to shrink the tube and set the epoxy resin. The heat shrink wrapping is then trimmed back to expose at least part of the epoxy resin coated thermistor, while maintaining electrical isolation of the bifilar wires. After heat treatment, the heat shrink has a wall thickness of around 10 µm.

As shown in the Figures, the thermography catheter is mounted on an angioplasty guide wire (not shown) which runs through the central lumen 14 and a guide member 17 which defines the tip of the thermography catheter.

In use, the apparatus may be actuated between a non-wall-temperature sensing configuration and a temperature sensing configuration. The non-temperature sensing configuration is hereinafter referred to as the retracted configuration. The temperature sensing configuration is hereinafter referred to as the deployed configuration. An example of the deployed configuration is shown in FIG. 2. An example of the retracted configuration is shown in FIG. 3.

In the retracted configuration, the sheath 16 encompasses the projections 11 so that they are constrained to lie parallel to the longitudinal axis of the catheter and therefore cannot take up a deployed position. The sheath 16 extends as far as the rear end of the guide member 17 but does not overlap the guide member. This minimises any protrusions from the thermography catheter which could lead to damage of the vascular wall. This is particularly important where a vessel is angulated or there is bifurcation of the vessel. Such features lead to bending of the thermography catheter and would emphasise any protrusions. Hence, in this example the sheath 16 and the guide member 17 present a smooth profile when adjacent to one another in the retracted configuration.

To adopt the deployed configuration, the sheath 16 is withdrawn away from the extreme distal tip i.e., away from the guide member 17, towards the proximal section, to expose the projections 11. When the sheath 16 is withdrawn to the extent shown in FIG. 2, the resiliently biased projections 11 take up the deployed configuration. It should be noted that the sheath is controlled from the proximal end of the apparatus and is not shown in its entirety in the Figures.

The projections 11 individually extend a certain distance (r) away from the longitudinal axis of the catheter. In the deployed configuration, r has a value in the range of 2–4 mm. However, r is not fixed and varies with the diameter of the vascular, tissue being measured due to the flexibility of the projections 11.

Different diameter catheters may be used for different diameters of vascular tissue. However, as it is desirable to minimize the diameter of catheters in all interventional vascular treatments, it is desirable to adapt the length of the projections and/or the angle to which the projections may extend away from the central lumen depending on the dimensions of the vascular tissue being measured rather than increasing catheter body dimensions. Thus, the projections for a large blood vessel, for example 8 mm diameter, will generally require a length of projection in the range of 5 mm to 10 mm. Smaller diameter vascular tissue, for example 2.5 mm diameter, will generally require a length of projection in the range of 2 mm to 6 mm. Typically, the ratio of the area of the cross-sectional profiles of the apparatus in the deployed to retracted configurations is up to 4:1.

The thermography catheter includes a valve system (not shown) allowing the annular gap between the sheath and the intermediate lumen to be flushed in an adequate way, thus minimising the possibility of air bubbles or debris within the sheath. Such a valve is constructed to enable engagement by a 2 mm, 5 mm, or 10 mm, 6° luer syringe. The thermography catheter may be flushed with a suitable fluid such as saline. When flushing the catheter, fluid should exit via the distal tip of the catheter, indicating proper flushing of the sheath. In addition, the catheter includes a female luer fitting (not shown) attached to the proximal end of the central lumen, to enable the central lumen to be flushed in a similar way to the sheath.

With reference to FIG. 4, in use, the sequence of events begins with the insertion of a guiding catheter into the area of general interest (step 100), for example the cardiac region. Where, for example, the coronary arteries are to be examined, the guiding catheter is inserted so that it is in or adjacent to the opening of the coronary arteries. An angioplasty guide wire is then inserted into the coronary artery, past the point of specific interest (step 110). The guide wire is usually inserted with the aid of standard fluoroscopic techniques, as is the guiding catheter. Once the guiding catheter and guide wire are in position, the thermography catheter of the present invention is maneuvered over the guide wire to a position beyond the specific area of interest in the coronary artery (step 120) with the aid of fluoroscopy.

An angiogram is taken (step 130) to assess the position of the thermography catheter in the vascular tissue. This image is saved and the position of the thermography catheter is marked on the image so as to define a starting point for the controlled pull-back step.

The guiding catheter is then locked in position and both the sheath and the lumen housed in the sheath are locked to mounts on the pull-back device. The sheath is then retracted to allow the projections to adopt the deployed configuration. Controlled pull-back of the thermography catheter then takes place (step 140). The pull-back takes place at a constant speed and is controllable by the user. Pull-back typically takes place at speeds of 0.1 to 2 mm in divisions of 0.1 mm or so.

The pull-back takes place over a distance of the vascular tissue being measured. Temperature readings may be taken intermittently or substantially continuously. The data transmitted by the sensors from the vascular wall is captured for data and image processing (step 150) together with a fluoroscopy/IVUS image frame.

As the thermography catheter is withdrawn inside the artery, the projections automatically adjust their angle following the wall's morphology without losing the desired thermal contact. The result is that the thermal contact between the sensors and the wall is continuously maintained, even when the catheter is crossing very irregular plaque formations.

Once the pull-back has been completed relative movement between the sheath and the intermediate lumen places the sensors in the retracted configuration. This restores the original smooth profile of the thermography catheter.

As mentioned above, the system software has the capability to capture image-frames that come from standard fluoroscopy or IVUS devices simultaneously with temperature. Spatial data that come from fluoroscopy/IVUS are combined by the software with temperature data. This is done as follows: Before the thermography procedure starts, and while the thermography catheter is still out of the target vessel, the user records the fluoroscopy-tube/bed position and records a video frame during injection of contrast media. The vessel is opacified, and the image is stored and projected on one of the system monitors. The user calibrates the pixel/mm relation by using the guiding catheter as a known reference so that distances in mm can subsequently be estimated accurately on the monitor.

Figure 5:

As shown in FIG. 5, the user then marks the beginning and ending of the area of interest (points B and E) by clicking on them using the mouse; in return, the software marks these points on the monitor by arrows or lines. The user then positions the thermography catheter in the target vessel by pushing it forward on the guide wire until the fluoroscopic marker on the thermography catheter passes point E over a few mm; while watching the system's monitor, the thermal sensors are then deployed and the user manually pulls the thermography catheter back gently until the fluoroscopic marker overlaps exactly on point E. The software then instructs the automatic pull-back device to pull back the thermography catheter over the length of the BE curve within the vessel.

The software then performs auto-border detection on the BE area of the fluoroscopy video frame using a photoluminescence technique, and temperature is subsequently coded in the atherosclerotic plaque outline as RGB color degradation from dark-blue (0,0,255) corresponding to the minimum detected temperature, to flashing red (255,0,0) corresponding to the maximum detected temperature. A reference color map may be provided, and by moving the mouse cursor inside the BE area, temperature values may also automatically be provided in a numeric format.

What is claimed is:

1. A catheter apparatus for temperature measurement of vascular tissue, comprising a flexible body, at least one resiliently biased projection depended from the body, a sensor carried by the projection and an electrical carrier for transmitting data from the sensor to a remote device, wherein the electrical carrier is coiled around the body of the projection in a manner so as to reduce strain when the projection flexes.

2. An apparatus according to claim 1, in which the pitch of the coil is arranged such that there are 5 to 10 turns per cm over the length of the projection.

3. An apparatus according to claim 1, further comprising a heat shrink wrapping applied around at least a portion of the length of the projection.

4. An apparatus according to claim 1, wherein the body has a longitudinal axis and at least part of the projection is extensible radially from the longitudinal axis of the catheter body.

5. An apparatus according to claim 1, wherein the body has a longitudinal axis and at least part of the projection is extensible radially from the longitudinal axis of the catheter body.

6. An apparatus according to claim 5, wherein the ratio of the area of the cross-sectional profiles of the apparatus in the retracted and deployed configurations is in the range 4:1–1.1:1, preferably 3:1–1.25:1, more preferably 2.5:1–2.0:1, most preferably 1.75:1–1.25:1.

7. An apparatus according to claim 1, further comprising multiple sensors and wherein the sensors are positioned circumferentially about a longitudinal axis of the catheter body.

8. An apparatus according to claim 1, wherein the sensor is a thermistor.

9. An apparatus according to claim 1, wherein the projections comprises a superelastic material.

10. An apparatus according to claim 1, further comprising a sheath adapted to substantially encompass the sensor in a retracted configuration.

11. An apparatus according to claim 10, wherein the sheath is retractable, thus enabling the projection to take up a deployed configuration.

12. An apparatus according to claim 1, wherein the projection, in a deployed configuration, adopts an arcuate shape along at least part of its length, and wherein the gradient of the arcuate portion of the projection, with respect to the longitudinal axis of the catheter, increases as a function of distance along the projection from the end attached to the catheter body.

* * * * *